US007630750B2

(12) United States Patent
Liang et al.

(10) Patent No.: US 7,630,750 B2
(45) Date of Patent: Dec. 8, 2009

(54) COMPUTER AIDED TREATMENT PLANNING

(75) Inventors: Zhengrong Liang, Stony Brook, NY (US); Bin Li, Centereach, NY (US); Dongqing Chen, Port Jefferson Station, NY (US); Eric E. Smouha, Northport, NY (US); Clemente T. Roque, Stony Brook, NY (US); Arie E. Kaufman, Plainview, NY (US); Mark R. Wax, Greenlawn, NY (US); Kevin Kreeger, East Setauket, NY (US)

(73) Assignee: The Research Foundation for The State University of New York, Stony Brook, NY (US)

( * ) Notice: Subject to any disclaimer, the term of this patent is extended or adjusted under 35 U.S.C. 154(b) by 1241 days.

(21) Appl. No.: 10/182,217

(22) PCT Filed: Feb. 5, 2001

(86) PCT No.: PCT/US01/03746

§ 371 (c)(1),
(2), (4) Date: Feb. 19, 2003

(87) PCT Pub. No.: WO01/56491

PCT Pub. Date: Aug. 9, 2001

(65) Prior Publication Data

US 2004/0015070 A1    Jan. 22, 2004

(51) Int. Cl.
*A61B 5/05* (2006.01)
(52) U.S. Cl. .................. 600/407; 382/128; 128/922
(58) Field of Classification Search .............. 600/416, 600/407, 424; 382/128; 128/920, 922; 345/418; 434/262, 272; 703/6, 11
See application file for complete search history.

(56) References Cited

U.S. PATENT DOCUMENTS 4,367,216 A    1/1983    Mutzel et al.

(Continued)

FOREIGN PATENT DOCUMENTS

WO    9613207    5/1996

(Continued)

OTHER PUBLICATIONS

Wang et al. Real-Time Interactive Simulator for Percutaneous Coronary Revascularization Procedures. Computer Aided Surgery 3:211-227 (1998).*

(Continued)

*Primary Examiner*—Brian Casler
*Assistant Examiner*—Jonathan G Cwern
(74) *Attorney, Agent, or Firm*—Dorsey & Whitney LLP

(57) ABSTRACT

A method of computer aided treatment planning is performed by generating and manipulating a three dimensional (3D) image of a region which includes at least one anatomical structure for which treatment, such as surgery, biopsy, tissue component analysis, prosthesis implantation, radiation, chemotherapy and the like, is contemplated. A virtual intervention, which simulates at least a portion of the contemplated treatment, is performed in the 3D image. The user can then determine the effect of the intervention and interactively modify the intervention for improved treatment results. Preferably, a warning is automatically provided if the intervention poses a risk of detrimental effect. The user can navigate through the contemplated region in the 3D image and assess the results. The treatment plans can be saved for comparison and post treatment evaluation.

40 Claims, 10 Drawing Sheets

U.S. PATENT DOCUMENTS

| | | | |
|---|---|---|---|
| 4,391,280 A | 7/1983 | Miller | |
| 4,630,203 A | 12/1986 | Szirtes | |
| 4,710,876 A | 12/1987 | Cline et al. | |
| 4,719,585 A | 1/1988 | Cline et al. | |
| 4,729,098 A | 3/1988 | Cline et al. | |
| 4,737,921 A | 4/1988 | Goldwasser et al. | |
| 4,751,643 A | 6/1988 | Lorensen et al. | |
| 4,791,567 A | 12/1988 | Cline et al. | |
| 4,823,129 A | 4/1989 | Nelson | |
| 4,831,528 A | 5/1989 | Crawford et al. | |
| 4,874,362 A | 10/1989 | Wiest et al. | |
| 4,879,668 A | 11/1989 | Cline et al. | |
| 4,984,157 A | 1/1991 | Cline et al. | |
| 4,985,834 A | 1/1991 | Cline et al. | |
| 4,985,856 A | 1/1991 | Kaufman | |
| 4,987,554 A | 1/1991 | Kaufman | |
| 4,993,415 A | 2/1991 | Long | |
| 5,006,109 A | 4/1991 | Douglas et al. | |
| 5,023,072 A | 6/1991 | Cheng | |
| 5,038,302 A | 8/1991 | Kaufman | |
| 5,047,772 A | 9/1991 | Ribner | |
| 5,056,020 A | 10/1991 | Feldman et al. | |
| 5,095,521 A | 3/1992 | Trousset et al. | |
| 5,101,475 A | 3/1992 | Kaufman | |
| 5,127,037 A | 6/1992 | Bynum | |
| 5,166,876 A | 11/1992 | Cline et al. | |
| 5,170,347 A | 12/1992 | Tuy et al. | |
| 5,187,658 A | 2/1993 | Cline et al. | |
| 5,204,625 A | 4/1993 | Cline et al. | |
| 5,229,935 A | 7/1993 | Yamagishi et al. | |
| 5,245,538 A | 9/1993 | Lis | |
| 5,261,404 A | 11/1993 | Mick et al. | |
| 5,265,012 A | 11/1993 | Amans et al. | |
| 5,270,926 A | 12/1993 | Tam | |
| 5,283,837 A | 2/1994 | Wood | |
| 5,295,488 A | 3/1994 | Lloyd et al. | |
| 5,299,288 A | 3/1994 | Glassman et al. | |
| 5,322,070 A | 6/1994 | Goodman et al. | |
| 5,345,490 A | 9/1994 | Finnigan et al. | |
| 5,361,763 A | 11/1994 | Kao et al. | |
| 5,365,927 A | 11/1994 | Roemer et al. | |
| 5,371,778 A | 12/1994 | Yanof et al. | |
| 5,442,733 A | 8/1995 | Kaufman et al. | |
| 5,458,111 A | 10/1995 | Coin | |
| 5,611,025 A | 3/1997 | Lorensen et al. | |
| 5,623,586 A | 4/1997 | Höhne | |
| 5,630,034 A | 5/1997 | Oikawa et al. | |
| 5,699,799 A | 12/1997 | Xu et al. | |
| 5,704,791 A * | 1/1998 | Gillio | 434/262 |
| 5,734,384 A | 3/1998 | Yanof et al. | |
| 5,782,762 A | 7/1998 | Vining | |
| 5,966,140 A * | 10/1999 | Popovic et al. | 345/441 |
| 5,971,767 A | 10/1999 | Kaufman | |
| 5,986,662 A | 11/1999 | Argiro et al. | |
| 6,130,671 A | 10/2000 | Argiro | |
| 6,148,095 A * | 11/2000 | Prause et al. | 382/131 |
| 6,219,059 B1 | 4/2001 | Argiro | |
| 6,236,878 B1 * | 5/2001 | Taylor et al. | 600/416 |
| 6,272,366 B1 | 8/2001 | Vining | |
| 6,464,639 B1 * | 10/2002 | Kim et al. | 600/443 |

FOREIGN PATENT DOCUMENTS

| | | |
|---|---|---|
| WO | 9811524 | 3/1998 |
| WO | 9837517 | 8/1998 |
| WO | 0055812 | 9/2000 |
| WO | 0055814 | 9/2000 |

OTHER PUBLICATIONS

He et al. Collision Detection for Volumetric Objects. Proceedings of the 8th IEEE Visualization '97 Conference.*

Hong et al., "3D Virtual Colonoscopy," 1995 Biomedical Visualization Proceedings, pp. 26-32 and 83 (1995).

Hong et al., "3D Reconstruction and Visualization of the Inner Surface of the Colon from Spiral CT Data," IEEE, pp. 1506-1510 (1997).

William E. Lorensen, "The Exploration of Cross-Sectional Data with a Virtual Endoscope," Interactive Technology and the New Health Paradigm, IOS Press, pp. 221-230 (1995).

Adam L. Penenberg, "From Stony Brook, a New Way to Examine Colons, Externally," The New York Times, p. 6 (1996).

David J. Vining, "Virtual Colonoscopy," Advance for Administrators in Radiology, pp. 50-52 (1998).

Zhou et al., "Three-Dimensional Skeleton and Centerline Generation Based on an Approximate Minimum Distance Field," The Visual Computer, 14:303-314 (1998).

Liang Z et al., "Inclusion of a priori information in segmentation of colon lumen for 3D virtual colonscopy", 1997 IEEE Nuclear Science Symposium Conference Record, pp. 1423-1427, vol. 2.

Valev et al., "Techniques of CT colongraphy (virtual colonoscopy)", Critical Reviews in Biomedical Engineering, 1999, Begall House, vol. 27, No. 1-2, pp. 1-25.

Shibolet O et al., "Coloring voxel-based objects for virtual endoscopy", IEEE Symposium on Volume Visualization, Research Triangle, Oct. 1998.

Kaufman A., Wan M., "Disobstruction of Colon Wall Collapse", Project Description, online www.cs.sunysb.edu, Jan. 1999.

Holzapfel G A, et al., "Large strain analysis of soft biological membranes: formulation and finite element analysis", Computer Methods in Applied Mechanics and Engineering, vol. 132, No. 1-2, pp. 45-61, 1996.

Kaye J. et al., "A 3D virtual environment for modeling mechanical cardiopulmonary interactings", CVRMED-MRCAS '97, pp. 389-398, 1997.

Burgard W. et al., "Active mobile robot localization by entropy minimization", Proceedings second euromicro workshop on advanced mobile robots, pp. 155-162, 1997.

Suya You et al., "Interactive volume rendering for virtual colonoscopy", Proceedings Visualization '97, pp. 433-436, 571.

Pai D.K. et al., "Multiresolution Rough Terrain Motion Planning", IEEE Transactions on Robotics and Automatic, vol. 14, No. 1, pp. 19-33, 1998.

Hagen H. et al., "Methods for Surface Interrogation", Proceedings of the Conference on Visualization, vol. CONF 1, pp. 187-193, 1990.

Chen et al., "Virtual Laryngoscopy: Feasibility Studies by CT and MRI", IEEE Medical Imaging Conference, Nov. 1999.

Chen et al., "MRI-Based Virtual Cystoscopy: The image segmentation and visualization", SPIE Conference, Feb. 12-18, 2000.

Chen et al., "A Fast Algorithm to Generate Centerline for Virtual Colonscopy", SPIE Conference, Feb. 12-18, 2000.

Richard Robb, "Virtual (Computed) Endoscopy: Development and Evaluation Using the Visible Human Datasets", Oct. 7-8, 1996. www.mayo.edu.

I. Bitter et al., "Penallized-Distance Volumetric Skeleton Algorithm", IEEE Transactions on Visualization and Computer Graphics, vol. 7, No. 3, Jul.-Sep. 2001, pp. 195-206.

M. Wan et al., "Distance-Field Based Skeletons for Virtual Navigation ", *Visualization 2001*, San Diego, CA, Oct. 2001.

M. Sato et al., "An automatic colon segmentation for 3D virtual colonoscopy ", IEICE Trans. Information and Systems, vol. E84-D, No. 1, Jan. 2001, pp. 201-208.

D. Chen et al., "A Novel Approach to Extract Colon Lumen from CT Images for Virtual Colonoscopy" IEEE Transactions on Medical Imaging, vol. 19, No. 12, Dec. 2000, pp. 1220-1226.

M. Wax et al., "Virtual Colonoscopy—CT Contrast Agent", Second International Symposium on Virtual Colonoscopy, Boston, MA, Oct. 2000.

K. Kreeger, et al., "Volume Rendering for Virtual Colonoscopy on an Affordable PC ", Second International Symposium on Virtual Colonoscopy, Boston, MA, Oct. 2000.

S. Lakare et al., "3D Digital Cleansing Using Segmentation Rays", IEEE Visualization 2000 Conference Proceedings, ACM/SIGGRAPH Press, pp. 37-44, Oct. 2000.

S. Lakare et al., "Automated Pre-navigation processing for Virtual Colonoscopy", Second International Symposium on Virtual Colonoscopy, pp., Oct. 2000.

D. Chen et al. "A tree-branch searching, multi-resolution approach to skeletonization for virtual endoscopy", SPIE Medical Imaging 2000, Feb. 2000.

M. Wan et al., "3D Virtual Colonoscopy with Real-time Volume Rendering", SPIE Medical Imaging 2000, Feb. 2000.

M. Wax et al., "Advancing Virtural Colonoscopy to Practice", International Workshop on 3D Imaging and Virtual Endoscopy, Feb. 2000.

W. Li et al., "Virtual Colonoscopy Powered by VolumePro", pp. 1-13, month unavailable 1999.

M. Wan et al., "Volume Rendering Based Interactive Navigation within the Human Colon", IEEE Visualization '99 conference, San Francisco, CA, Oct. 1999, pp. 397-400.

R. Chiou et al., "Interactive Fly-Path Planning Using Potential Fields and Cell Decomposition for Virtual Endoscopy", IEEE Trans. Nuclear Sciences, vol. 46, No. 4, Aug. 1999, pp. 1045-1049.

R. Chiou et al., "Volume Segmentation and Rendering of Mixtures of Materials for Virtual Colonoscopy", SPIE Medical Imaging '99, Feb. 1999, pp. 133-138.

Z. Liang et al., "On Segmentation of Colon Lumen for Virtual Colonoscopy", SPIE Medical Imaging, Feb. 1999, pp. 270-278.

Z. Liang et al., "Virtual Endoscopy in Early Detection of Cancers", Biomedical Imaging Symposium: Visualizing the Future of Biology and Medicine, Washington, D.C., Feb. 1999.

R. Chiou et al., "Unified Analysis, Modeling, Matching and Synthesis for CT Color Texture Mapping from the Visible Human Dataset", The Second Visible Human Project Conf., Bethesda, MD, Oct. 1998.

M. Wan et al., "Boundary Cell-Based Acceleration for Volume Ray Casting", Computer & Graphices, vol. 22, No. 6, 1998, pp. 715-721.

R. Chiou et al., "Interactive Path Planning for Virtual Endoscopy", Conf. Record IEEE NSS-MIC, Nov. 1998.

M. Wax et al., "Electronic Colon Cleansing for Virtual Colonoscopy", Presentation at the first Int'l. Conf. on Virtual Colonoscopy, Boston, MA, Oct. 1998.

L. Hong et al., "Virtual Voyage: Interactive Navigation in the Human Colon", Proc. ACM SIGGRAPH '97, Aug. 1997, pp. 27-34.

A. Viswambharan et al., "Virtual Colonoscopy: Three-dimensional Reconstruction of the Mucosal Surface of the Colon", Conf. of Radiological Society of North America (RSNA), Dec. 1996, pp. 565 (Scientific Merit Award).

L. Hong et al., "Physcially-Based Interactive Navigation", Technical Report TR.96.01.09, Computer Science Department, SUNY at Stony Brook, Jan. 1996.

L. Hong et al., "Visible Human Virtual Colonoscopy", Conference of National Library of Medicine Visible Human Project, Oct. 1996, pp. 29-30.

$80^{th}$ Scientific Assembly and Annual Meeting Nov. 27-Dec. 2, 1994, Radiology Society of North America Founded in, InfoRAD Exhibits.

Taosong He, et al. "Collision Detection for Volumetric Objects", Proceedings of the $8^{th}$ IEEE Visualization Conference, 1997 1070-2385/97.

Yaoping Wang et al., "Real-Time Interactive Simulator for Percutaneous Coronary Revascularization Procedures", Computer Aided Surgery, 3:211-227, 1998.

* cited by examiner

COMPUTER AIDED TREATMENT PLANNING

STATEMENT OF GOVERNMENT RIGHTS

This invention was made with government support under grant number CA 079180 awarded by the National Institutes of Health. The government has certain rights in the invention.

FIELD OF THE INVENTION

The present invention relates generally to surgical planning and more particularly relates to a system and method of using three dimensional interactive computer visualization in surgical planning, optimization and evaluation.

BACKGROUND OF THE INVENTION

In many areas of medical treatment, it would be beneficial for a medical practitioner to be able to visualize a region for which treatment is contemplated and to accurately simulate the contemplated treatment. By visualizing the effect of the simulated treatment and altering the proposed treatment to optimize the results in a virtual setting, results can be improved and risks associated with the actual treatment can be reduced. This is particularly true in the case of invasive procedures such as surgery, biopsies and prosthesis implantation. The virtual setting would serve both as a tool for the guidance for actual treatment and as a "gold standard" for evaluation of the actual treatment and for follow up management.

The ear is a specialized organ for which the computer aided treatment planning is expected to play a valuable role. The ear is an internal organ that is difficult to examine because it is encased in the temporal bone. The ear also contains important anatomic structures, including the hearing bones (ossicles), inner ear organs of hearing and balance, and facial nerve. Congenital aural atresia (CAA) is a congenital developmental anomaly of the middle ear that manifests with varying degrees of external auditory canal stenosis or atresia, ossicular derangements, poorly developed mastoid and tympanic cavities. This disease results in conductive hearing loss which can be severe. In some cases, however, CAA can be treated surgically. However, because of the complex anatomy of the ear and the risks associated with this surgical procedure, such as facial paralysis, thorough surgical planning is required to assess and maximize the likelihood of successful surgery.

Preoperative imaging, such as by computerized tomography (CT), is considered an important element in surgical planning. Conventional two-dimensional (2D) CT images demonstrate the key anatomic structures of the ear, including the stapes, middle ear space, inner ear and facial nerve. However, the 2D CT is limited in its ability to represent the spatial relationships between these important structures. For example, an aberrant facial nerve, a retro-displaced temporamandibular joint, or a low-lying tegmen tympani might make surgical reconstruction difficult or impossible. Three-dimensional (3D) information would be very helpful for planning surgical therapy for treating congenital aural atresia and other forms of ear pathology.

Traditionally, spatial anatomical relationships could only be surmised by mentally integrating sequential 2D CT scan images. However, the advent of 3D computer graphical visualization techniques and high-resolution CT scanning now allow 3D images (either surface-based or volume-based) to be constructed from sequential scan images and be displayed on a computer screen. Three-dimensional relationships between adjacent organs can be shown by interactively manipulating these virtual organs on the screen using a mouse or some other interactive devices. Over the past decade, many applications of such techniques in a number of areas of medicine, including otology, have been explored.

The article "Three Dimensional CT Scan Reconstruction for the Assessment of Congenital Aural Atresia" by Andrews et al., which was published in the American Journal of Otology, Vol. 13, Num. 13, May 1992, discusses generating 3D computer images from 2D CT data to aid a surgical planning of CAA. This paper demonstrates that the structures of the ear can be successfully rendered to assist the surgeon in visualizing the spatial relationships among the critical structures of the ear, such as the facial nerve, mandibular condyle, the locations and thickness of the atretic plate and the like. The system disclosed by Andrews et al., provided a useful 3D image of the anatomy of the ear. However, due to the complexities of the anatomy of the ear, additional computer-aided planning and "virtual surgery" features to confirm the surgical plan would also be desirable.

Accordingly, there remains a need for improved medical treatment planning tools for optimizing the procedures and for evaluating the results.

SUMMARY OF THE INVENTION

It is an object of the present invention to provide a system for computer aided treatment planning that employs 3D surface and volume rendering and a virtual intervention feature to confirm the proposed treatment plan.

It is another object of the present invention to provide a system for computer aided treatment planning that provides warnings to a user if a proposed intervention presents risk of damage to surrounding structures.

A method of computer aided treatment planning in accordance with the invention includes generating a 3D image of a region which includes at least one anatomical structure for which treatment is contemplated. A virtual intervention is applied to the region of the 3D image to simulate at least a portion of the contemplated treatment. The effect of the intervention, in terms of both efficacy and potential risk or collateral damage, can be assessed and the intervention can be interactively modified for improved treatment results. When the intervention plan is finalized, the user can navigate within the 3D image in the area where the intervention is applied to fully visualize the results of the intervention. The intervention plan can also be saved in computer readable storage for later use as a "gold standard" for evaluating the completed intervention at later dates.

The present method is applicable generally to treatment planning, including surgical planning, virtual biopsy, and prosthesis implantation.

In one application, the planning of surgery to correct aural atresia, the region in the image includes the ear and the at least one anatomical structure includes at least one of the temporal bone, facial nerve, and stapes. In this case, the virtual intervention includes the placement of a virtual cylinder representing the location where an external auditory canal may be formed. In determining the effect of the virtual intervention, the proximity of the virtual cylinder to anatomical structures of the ear is measured and a warning can be provided if the proximity is less than a predetermined threshold distance. The step of modifying the intervention for this application includes changing the position and/or size of the virtual cylinder.

Preferably, once the final position of the virtual cylinder is determined, a virtual drilling operation can be performed by removing the volume within the virtual cylinder and navigating through the region in the 3D image. The stages of placing an intervention, modifying the intervention, virtually performing the intervention and navigating through the results are both interactive and repeatable. Each plan can be stored in computer readable media as an entry in a database for future retrieval, examination and comparison.

The manipulation of the 3D image can be costly and processor intense. Preferably, the step of generating the 3D image of a region includes acquiring a set of 2D images of a region; applying segmentation to extract structures of interest; converting the 2D images to a voxel based dataset of region; storing the voxel based dataset in a partitioned data structure; and rendering the 3D image from the voxel based dataset. The partitioned data structure can take the form of a binary space partitioning (BSP) tree having a number of leaf nodes where the voxels of the voxel based dataset are stored. Using this form of data structure, the step of applying the intervention can preferably include: identifying those leaf nodes which are effected by the intervention; applying the intervention to the effected leaf nodes to launch voxel based constructive solid geometry (CSG) operation and image regeneration; and re-rendering only the portions of the 3D image associated with the effected leaf nodes. In this way, the aforementioned processing burden can be reduced. In addition, voxel-based constructive solid geometry (CSG) subtraction and level-of-detail rendering can also be used to reduce the processing burden.

Preferably, re-rendering can take place based on a simplified level of detail (LOD) rendering mode. The CSG operation preferably includes converting the virtual cylinder into a voxelized format and performing a voxel-based CSG subtraction between the virtual cylinder and the tissue bounded by the virtual cylinder volume.

The method of computer aided treatment planning can be used in connection with numerous contemplated treatments, such as biopsy. In this case, the intervention is the placement of a virtual biopsy needle into a targeted position where highly suspicious tissue resides within the region. A warning can be provided if the virtual biopsy needle is outside the targeted position. A warning can also be provided if the proposed path of the biopsy needle will damage anatomical structures in the vicinity. In the case of a biopsy, the virtual biopsy needle can be modeled as a virtual cylinder. The tissue within the volume of the virtual cylinder can be removed from the region, examined in a separate display such as by texture analysis, and geometric features of the tissue, and then reinserted into the region, if desired. Virtual biopsy can be used in numerous applications, including the planning for examining pulmonary nodules, prostate tissue abnormality and breast cell calcification.

Virtual biopsy can differentiate among tissue types using geometric feature analysis, texture analysis and/or tissue density analysis to determine the types of cells which are within the region of tissue extracted by the virtual biopsy needle.

Yet another application of the present method is in the implantation of prosthesis or stent grafts. In this case, the virtual intervention includes the removal of damaged tissue in the targeted vicinity of an implant. A virtual model of the implant can be optimized from an analysis of the targeted vicinity. The pathway for the insertion of the implant can be modeled as a generalized virtual cylinder. A warning can be provided if the generalized virtual cylinder placement will damage critical anatomical structures. The virtual model can be used to generate the actual insert. In addition, the resulting plan can be saved in a database for follow post-treatment evaluation of the actual intervention. Implants can take on various forms, such as cochlear implants, stent grafts and the like.

The virtual cylinder is a generalized virtual volume which has the parameters of the tool it is simulating. In the case of the surgical planning for aural atresia, the tool is a drill bit and the virtual cylinder is a simple cylinder with a length, and circular cross section. However, the term virtual cylinder is not so limited. The diameter can vary as can the cross section and contour along the long axis. In addition, the virtual cylinder may be a deformable model, such as, for example, when the tool being modeled is a flexible catheter.

Yet another application of the present method is in the planning of carotid plaque analysis and intervention. In this case, the intervention includes the analysis of the plaque component on the arterial wall and the size and removal of plaque in a targeted vicinity. A virtual model of the plaque can be optimized from an analysis of the targeted vicinity. The pathway for the removal of the plaque can be modeled as a generalized virtual cylinder. A warning can be provided if the generalized virtual cylinder has a size or placement which will be ineffective at extracting the plaque if the plaque has a high risk of rupture or dislodgement in the present placement. The virtual model can be used to generate the arterial insert which will be used in the actual operation. In addition, the resulting plan can be saved in a computer database for future reference and post-treatment evaluation.

A system for computer aided treatment planning includes a scanner, such as a CT or MRI scanner, for acquiring image data from a patient. A processor is provided which receives the image data and generates a 3D, voxel based dataset representing at least a portion of the image data. A display, such as a liquid crystal display (LCD) or Cathode Ray Tube (CRT) is operatively coupled to the processor and provides a 3D representation the image data from the voxel based dataset. A user interface device, such as a mouse or trackball, is operatively coupled to the processor and allows a user to manipulate the image on the display. Computer readable memory is operatively coupled to the processor and has a computer program stored therein. The computer program directs the processor to perform the steps of: applying a virtual intervention in the region of the 3D image in response to a signal from the user interface device; analyzing the intervention and automatically generating a warning indication if the intervention results in a high degree of risk arising. Previewing a contemplated treatment virtually, through the user interface, the user can modify the intervention to eliminate the warning.

BRIEF DESCRIPTION OF THE DRAWING

Further objects, features and advantages of the invention will become apparent from the following detailed description taken in conjunction with the accompanying figures showing illustrative embodiments of the invention, in which.

Figure 1:
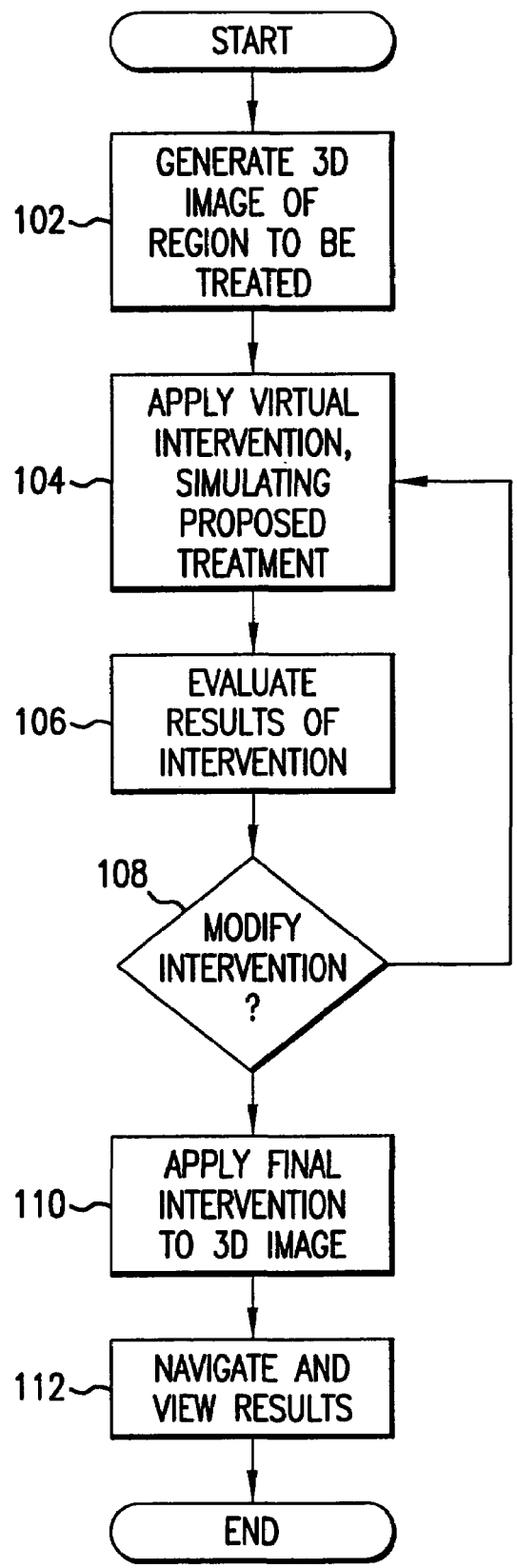
FIG. 1 is a simplified flow diagram illustrating an overview of present method for computer aided treatment planning.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF PREFERRED EMBODIMENTS

Figure 2:
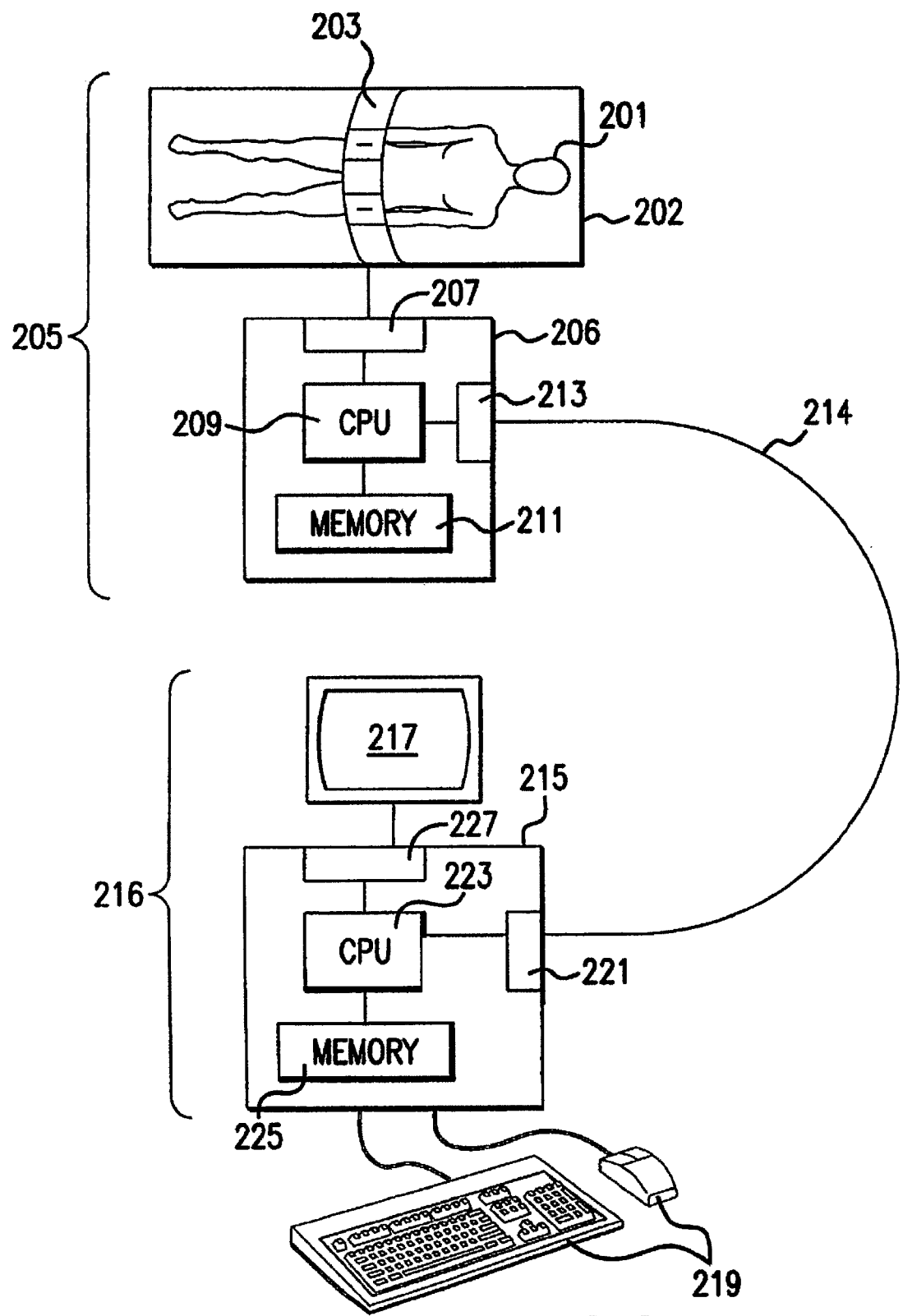
FIG. 2 is a simplified block diagram of a system suitable for performing the present method of computer aided treatment planning.

FIG. 1 is a flow chart which illustrates an overview of the present method of computer aided treatment planning which is generally performed on a computer based system, such as that illustrated in FIG. 2. The invention will be described in terms of medical applications performed on human patients and in the context of medical treatment, such as surgery, prosthesis implantation, biopsy, medication, therapeutic radiation, therapeutic ultrasound and the like. It will be appreciated, however, that the invention is not limited to human patients, nor to the exemplary list of treatments referenced. The term treatment is used to mean an intervention in a region, such as but not limited to tissue, that is intended to effect an alteration of the region.

Referring to FIG. 1, the method includes the initial step of generating a three dimensional (3D) image representation of a region for which some form of medical treatment or intervention is contemplated (step 102). Generating such a 3D image representation generally involves acquiring a sequential series of 2D images, such as from a spiral computed tomography (CT) scanner or magnetic resonance imaging (MRI) scanner and transforming this 2D image data into a volumetric data set which provides a 3D representation of the region on a 2D display, such as a computer monitor. Such a technique is well known in the art, and is discussed, for example in U.S. Pat. No. 5,971,767 to Kaufman et. al., which is hereby incorporated by reference in its entirety.

After the 3D image is presented to a user, such as a physician, some form of virtual intervention, which simulates at least a portion of a proposed treatment, is applied to the 3D image (step 104). The virtual intervention can take on several forms, such as the removal of tissue or artery plaques, the repair or reconstruction of a diseased or malformed organ, the placement of a prosthetic implant, the placement of a stent graft, the placement of biopsy needle, the placement of therapeutic radiation and the like.

Using the resulting 3D image, and possibly the assistance of computer generated models of the applied intervention, the results of the virtual intervention can be evaluated and warnings can be generated indicative of high levels of risk attendant with the proposed intervention (step 106). Based on the displayed results, and any warnings provided, the user can repeatedly modify the proposed intervention (step 108) and apply the modified intervention to the 3D image (step 104) until a satisfactory result is ascertained or it is determined that the proposed treatment is not feasible. Several alternative interventions can be saved in a database to compare the risks and efficacy of proposed alternative intervention plans.

After the proposed intervention is finalized, the final intervention can be simulated and the results fully applied to the 3D image (step 110). The user can then view the results and navigate in and around the region to determine the efficacy of the proposed treatment (step 112). The planned results can then be used as a guide for the actual treatment with coordinate registration between the virtual model and the patient and as a gold standard to evaluate the actual intervention during post-intervention follow up examinations.

FIG. 2 is a simplified diagram of an exemplary system for performing the present computer aided treatment planning methods. In this exemplary embodiment, a patient 201 lies down on a platform 202 while scanning device 205 scans the area that contains the organ or organs which are to be examined. The scanning device 205 contains a scanning portion 203 which acquires image data of the patient and an electronics portion 206. Electronics portion 206 generally includes an interface 207, a central processing unit 209, a memory 211 for temporarily storing the scanning data, and a second interface 213 for sending data to the virtual navigation platform. Interface 207 and 213 can be included in a single interface component or can even be the same component. The various operational components and subsystems in electronics portion 206 are connected together with conventional connectors.

The data from the scanning portion 203 is generally in the form of a stack of two dimensional image slices of a region of interest, which are provided from conventional spiral computed tomography (CT) and magnetic resonance imaging (MRI) scanners. Central processing unit 209 converts the scanned 2D data to a 3D voxel data representation, in a manner known in the art, and stores the results in another portion of memory 211. Alternatively, the converted data can also be directly sent to interface unit 213 to be transferred to the virtual navigation terminal 216. The conversion of the 2D data could also take place at the virtual navigation terminal 216 after being transmitted from interface 213. Preferably, the converted data is transmitted over carrier 214 to the virtual navigation terminal 216 in order for an operator to perform the computer aided treatment planning. The data can also be transported in other conventional ways such as storing the data on a storage medium and physically transporting it to terminal 216 or by using satellite transmissions.

The scanned data need not be converted to its 3D representation until the visualization rendering engine requires it to be in 3D form. This may save computational steps and memory storage space.

Virtual navigation terminal 216 includes a screen 217 for viewing the image data, an electronics portion 215 and interface device 219 such as a keyboard, mouse or track ball. The electronics portion 215 generally includes a interface port 221, a central processing unit 223, other components 227 necessary to run the terminal and a memory 225. The components in terminal 216 are connected together with conventional connectors. The converted voxel data is received in interface port 221 and stored in memory 225. The central processor unit 223 then assembles the 3D voxels into a virtual representation which can be displayed on screen 217. Preferably, a graphics accelerator which is optimized for volume rendering can also be used in generating the representations. The virtual navigation terminal 216 can be embodied using a high speed graphics work station, such as manufactured by Silicon Graphics, Inc., or in a high speed personal computer, such as an IBM compatible computer with a Pentium III (or higher) processor having a 1 GHZ or faster clock speed.

The operator can use interface device 219 to interact with the system 200, such as to indicate which portion of the scanned body is desired to be explored. The interface device 219 can further be used to control the image being displayed, including the angle, size, rotation, navigational position and the like.

Scanning device 205 and terminal 216, or parts thereof, can be part of the same unit. Numerous CT and MRI systems are suitable for such applications. A single platform may be used to receive the scanned image data, convert the image data to 3D voxels if necessary and perform the guided navigation.

The method of FIG. 1, while applicable generally to numerous treatment planning operations, will now be described in further detail in the context of surgical planning for the treatment of aural atresia. The surgical repair of aural atresia consists of several steps: drilling a new external auditory canal in the temporal bone; creating a new meatus in the concha; forming a new eardrum using temporalis fascia; and re-lining the bony canal with a skin graft. An important aspect of surgical planning in this regard is to define an acceptable path for the new auditory canal from the outer cortex to the inner ear and to visualize the important internal structures of the ear, including the relative spatial relationships among these structures.

The present method of medical treatment planning provides for 3D imaging of the structures of the ear and allows interactive positioning of a virtual drilling site which will form the external auditory canal in the temporal bone. Using computer aided planning, this canal can be placed, analyzed and repositioned if necessary. If a number of proposed plans are acceptable, several variants can be saved in a database for comparison. Once the final location is accepted, then a virtual drilling operation can be performed to determine if the planned surgery is likely to be successful. Once the canal is virtually drilled, the user can navigate into and through the canal and visualize the surrounding structures of the ear. The operation is interactive and repeatable. The plan can be stored in the database and the surgeon can then compare different plans for the same case which have been stored in the database and choose the best available plan.

Figure 3:
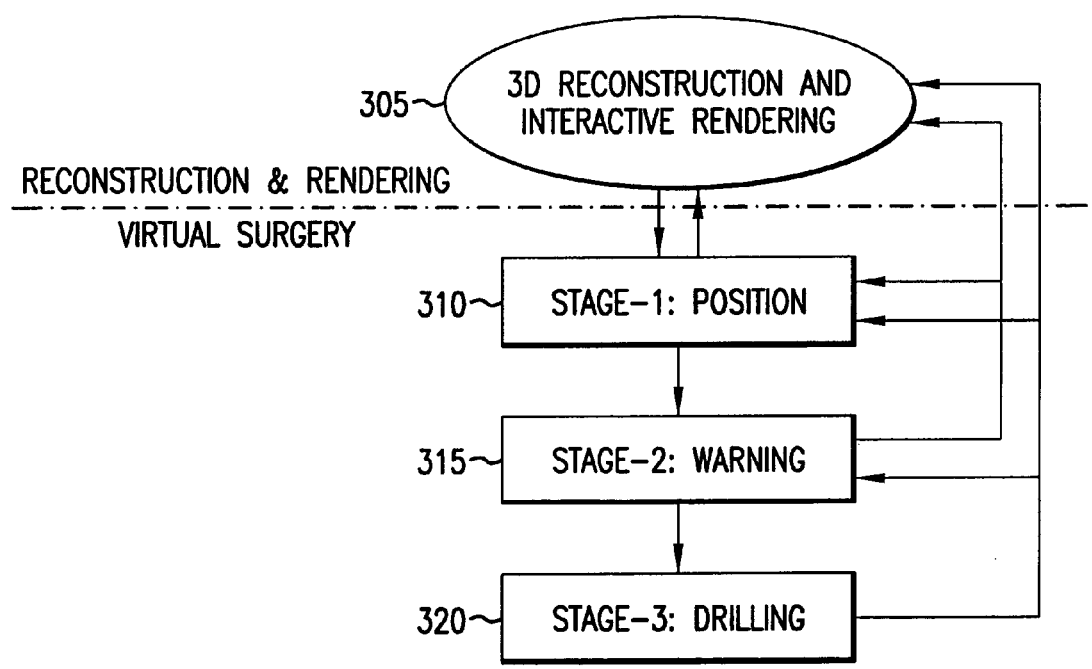
FIG. 3 is a simplified flow diagram illustrating an overview of exemplary rendering and virtual surgery steps used in the present method in the planning of treatment for aural atresia.

FIG. 3 is a flow chart illustrating an overview of the present method for performing surgical planning in the context of treating aural atresia. In this case, the primary intervention that the user, generally a surgeon, will undertake is the creation of a new external auditory canal which must be drilled through the temporal bone. Initially, a 3D rendering of the important structures of the ear is created using acquired 2D image scan data, such as from an MRI scan or CT scan (step 305). Because the various structures of the ear present a similar image intensity in the image scan data, it is preferable that the 3D rendering step include an image segmentation process to distinguish the various tissue types of the ear, such as the facial nerve, temporal bone and the like. From the segmented image data, a volume based rendering can be presented to the user, such as on a computer display, where the various structures of the ear are delineated, as is illustrated in FIG. 8.

Figure 8:
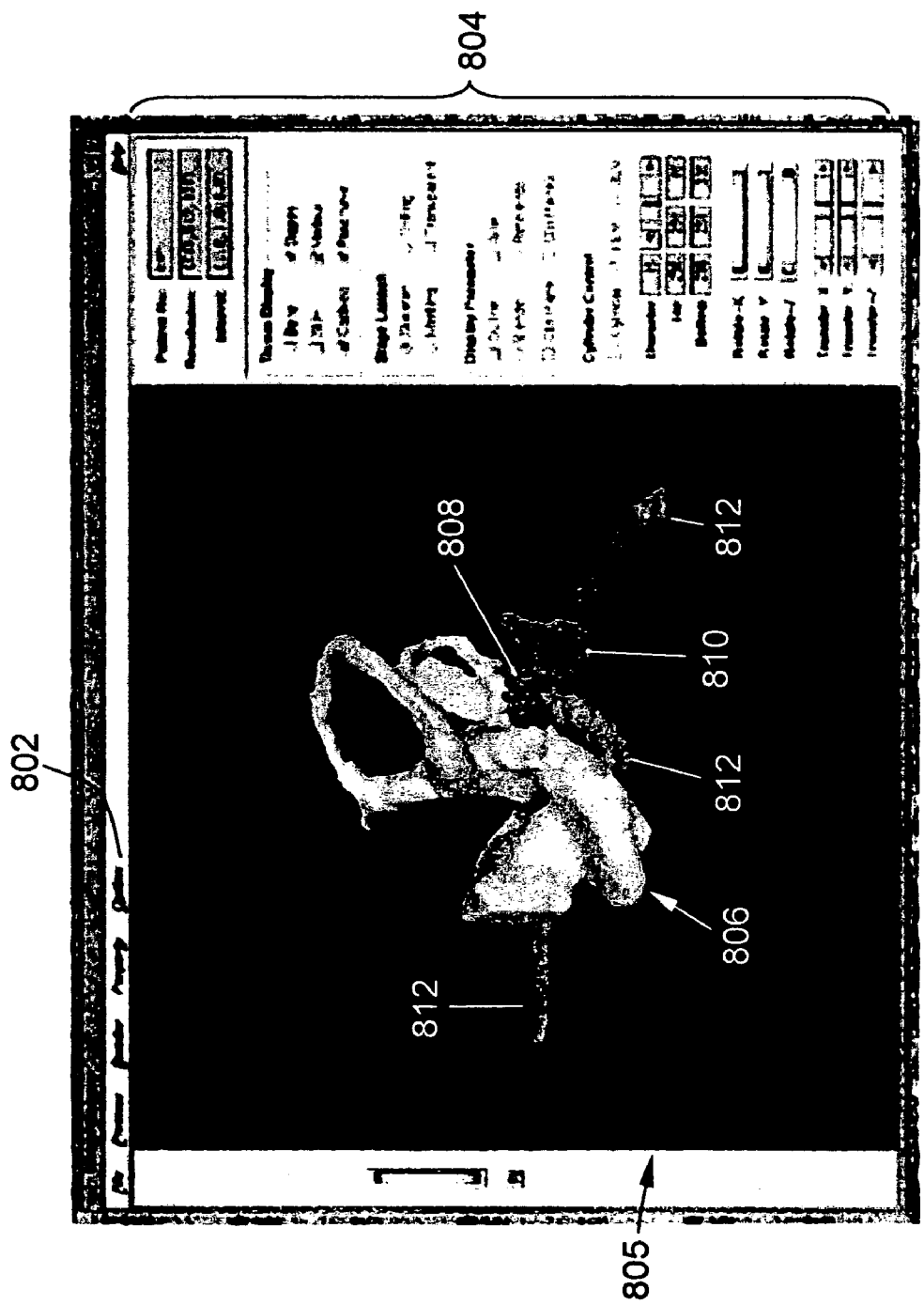
FIG. 8 is a graphical representation of an exemplary screen display illustrating a 3D rendering of the structures of the ear with background tissue and the temporal bone not shown.

FIG. 8 is an exemplary system display which could be observed by the user on terminal 217. The display preferably takes the form of a graphical user interface (GUI) which allows the image to be fully manipulated on the display by the user operating the user interface device 219. The top of the display includes a tool bar 802, where commonly used commands can be readily referenced, in a manner known in the art. The right hand portion of the display shows a user interface portion 804, where image parameters can be observed and manipulated. The main display portion 805 illustrates the segmented image data showing the various structures of the ear including the cochlea 806, stapes 808, malleus 810, and the facial nerve 812. The user can manually edit the segmented small structures, if the user desires to improve the segmentation results. By altering the transfer function used in the volume rendering process, the user can control the color and opacity of each of the structures. The user can also control non-geomtetry properties of each structure, such as shading, color and opacity. For example, as in the view shown, the user can render the temporal bone transparant to view the underlying anatomy of the ear. Alternatively, the temporal bone could be rendered transparent, such that the underlying anatomic structures could be viewed through the outline of the temporal bone such that the spatial relationship among these structures could be observed.

Figure 9:
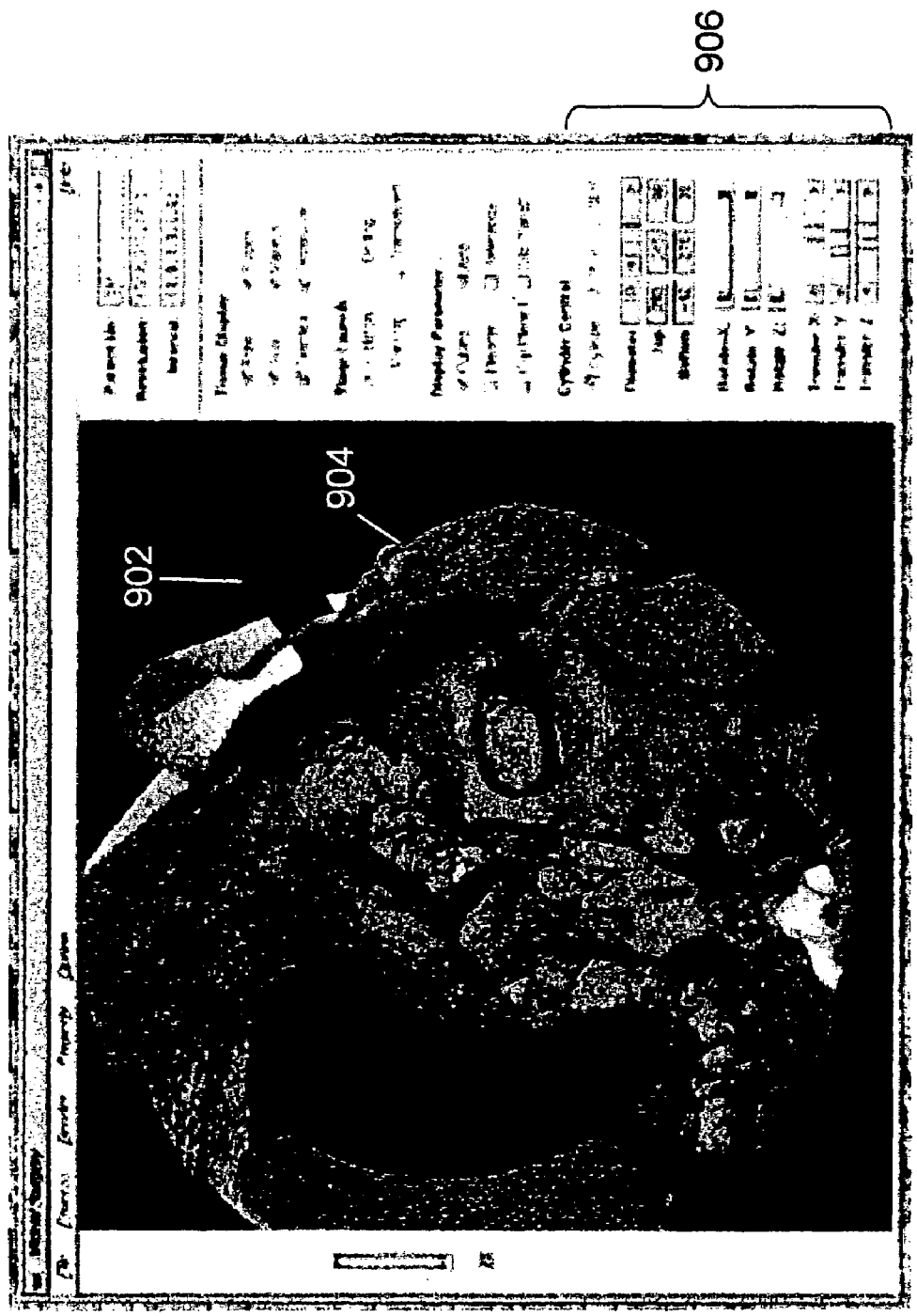
FIG. 9 is a graphical representation of an exemplary screen display illustrating a 3D rendering of the structures of the ear and illustrating the placement of a virtual cylinder as part of a surgical planning procedure for treating aural atresia.

As shown in FIG. 9, a 3D cylinder is used as the model for the drill bit which a surgeon will use to form the external auditory canal. This cylinder 902 is interactively placed by the user in a position which is expected to open a passage through the temporal bone 904 from the outer bony cortex toward the middle ear (step 310). The user can manipulate the length, diameter and position of the cylinder using the interface device 219 to drag the cylinder or by changing the parameters numerically in the cylinder control area 906 of the interface portion 804 of the display. The computer system then illustrates the placement of the cylinder, such as by displaying this region as a different color. By altering the opacity of the objects through which the cylinder 902 projects, the proximity of the cylinder to the structures of the inner ear can be clearly observed, such as is illustrated in FIG. 10.

The computer aided treatment terminal 216 can analyze the proximity of the cylinder in this initial placement to the critical structures surrounding the proposed drilling site, such as the facial nerve and ossicles, and issue warnings if drilling would result in potential damage to these structures (step 315). Based on the visual representation and the warnings that are presented, the user can alter the proposed intervention, such as by repositioning the cylinder, until a satisfactory path for the cylinder is determined or it is determined that the proposed treatment is not feasible. The user can also control the length and diameter of the cylinder to conform to different drilling depths and drill diameters, respectively. Once such a path has been determined, a virtual drilling operation can be performed by removing the region represented by the cylinder from the image (step 320). Of course, there may be more than one acceptable course of intervention. Accordingly, variations in the plan can be implemented and saved in a database such that alternatives can be compared and the best acceptable alternative may be selected.

Figure 11:
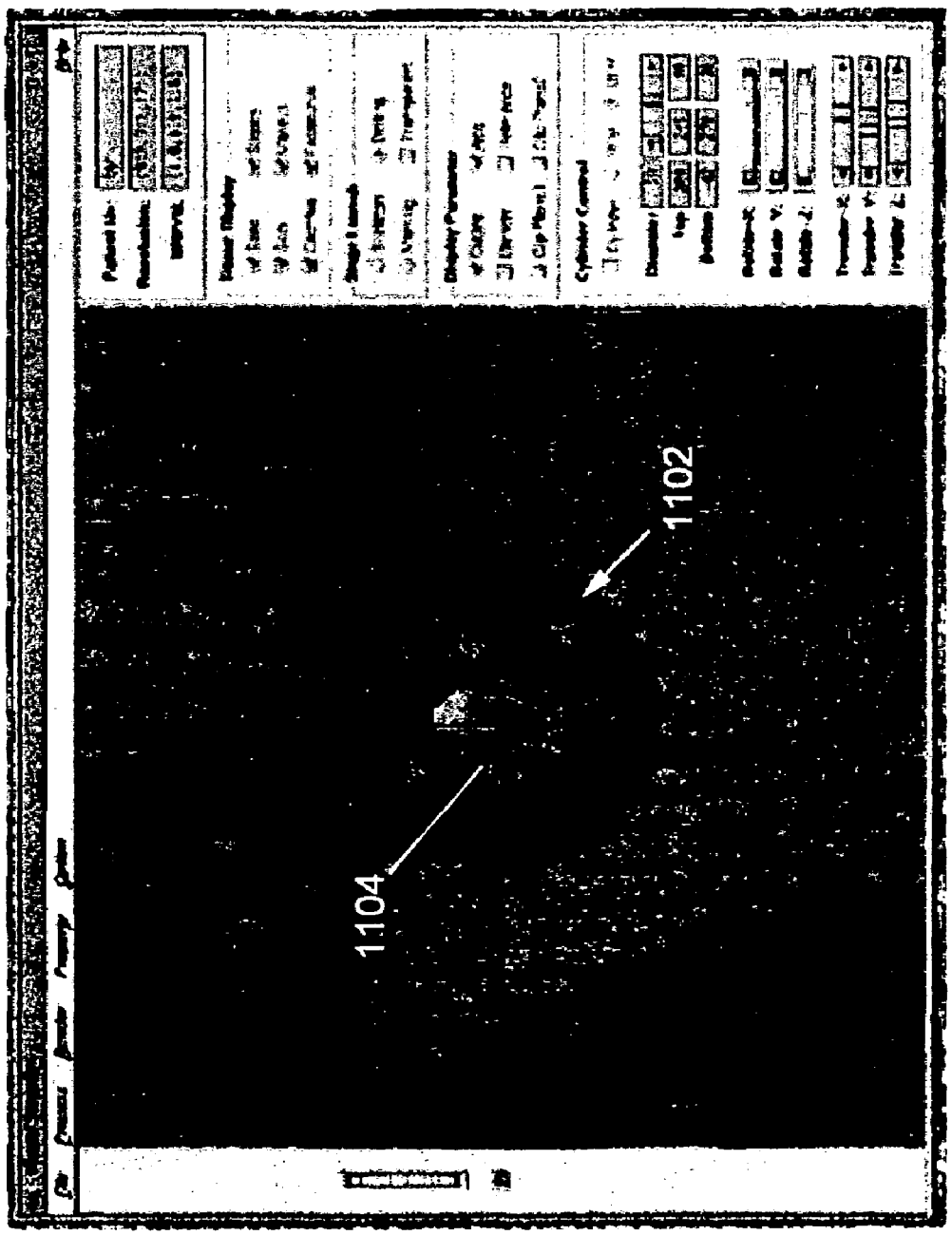
FIG. 11 is a graphical representation of an exemplary screen display illustrating a 3D rendering looking down and through the auditory canal that is formed by performing a virtual drilling operation to remove the tissue occupied in the volume of the virtual cylinder.

During and after the virtual drilling operation, the user can navigate through the bore of the drill site to visualize, from within the treated area, the efficacy and/or risks of the treatment (step 305). As illustrated in FIG. 11, when the virtual drilling operation is complete, the user can navigate completely through the new auditory canal 1102 and, at the exit point, visualize the spatial relationship of the newly formed canal with respect to the inner ear structures, such as the ossicular mass 1104. During any visualization step, the colors of the objects being viewed, as well as the relative opacity of the objects, can be varied by the user to present different views of the region.

Figure 10:
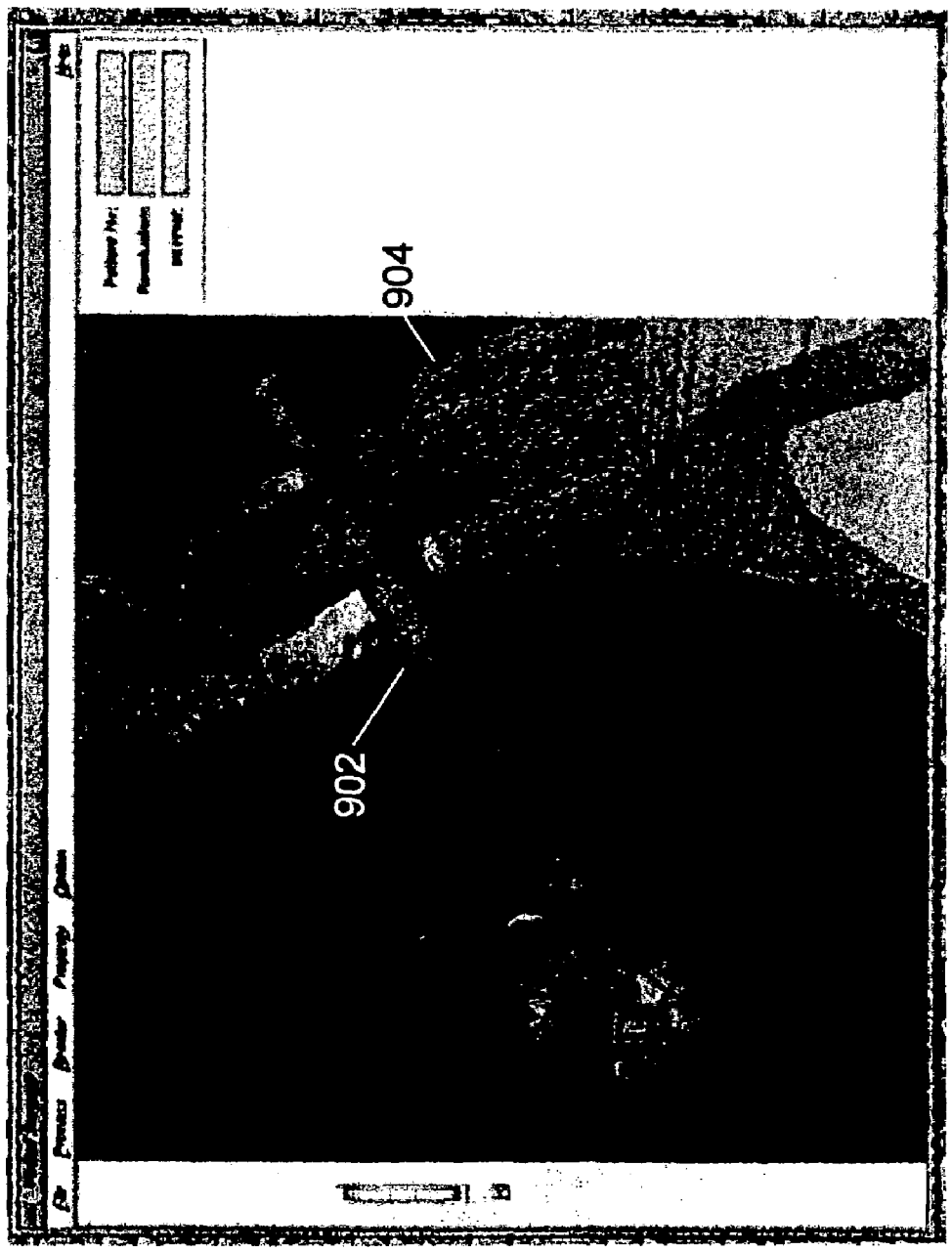
FIG. 10 is a graphical representation of an exemplary screen display illustrating a 3D rendering of the structures of the ear and further illustrating the placement of a virtual cylinder as part of a surgical planning procedure for treating aural atresia.

The virtual cylinder 902 is illustrated in FIGS. 9 and 10 as a simple cylinder having a circular cross section and a long axis. This simple model is a reasonable representation of the rigid drill bit used in the aural atresia surgical procedure. However, it will be appreciated, that the virtual cylinder need not be a simple cylindrical model and that it can and should be sized and shaped to conform to the size and shape of the instrument that will be used to perform the contemplated treatment. The virtual cylinder need not have a circular cross section nor a constant diameter. For example, if the tool is generally shaped as a curved rod, a cylindrical model which is curved along its major axis would be appropriate. For a complex tool with articulated joints and extensible members, a more complex "virtual cylinder" model can be used. In addition, the generalized virtual cylinder can be modeled as a deformable object to fit in a specific anatomical environment and to model flexible tools, such as catheters. Regardless of the actual model employed, the principle of the method remains the same.

A difficulty encountered in the imaging step 305 is that several of the relevant anatomical structures have similar intensity values on the CT image. This, in combination with the complex anatomy of the ear, can make it difficult to distinguish the various structures. To address this problem, a two-level image segmentation process can be employed. The two-level segmentation process involves low-level processing of the voxels in the region of interest followed by high-level organ extraction. During the low-level processing, the voxels of the 3D dataset are clustered into groups based on an intensity feature of the voxels, which can be measured by an associated local intensity value vector. This can be determined using a modified self-adaptive on-line vector quantization algorithm, such as is described in the article "A self-adaptive on-line vector quantization algorithm for MRI segmentation," by Chen et al. in the proceedings of The 7th Scientific Meeting of ISMRM, May 1999, Philadelphia, which is hereby incorporated by reference. In the low-level classification, each voxel is associated with a local vector which is defined in 3D space. From the local vectors, a feature vector series can be derived using a components analysis which is well known in the art. The feature vectors are then clustered using a self-adaptive on-line vector quantization algorithm. The voxels are then grouped according to the classification of their feature vectors and are assigned an integer value representing this classification.

After the low-level processing is complete, the high level organ extraction processing can follow. Initially, a user locates a seed, or starting point, within regions representative of soft tissue, bone and air spaces. The system then applies a region growing algorithm starting from the seed points to extract the anatomical features of the ear, such as the temporal bone, stapes, ossicles and facial nerve.

The temporal bone, which presents high contrast compared to the surrounding tissue is fairly easy to automatically segment. However, certain structures, such as the inner ear and facial nerve, may require addition user input to fully delineate these structures. For example, the soft tissue of the inner ear presents a similar intensity value on CT images as compared to the surrounding soft tissue. Thus, to insure proper extraction of this feature, it may be desirable for the user to manually delineate the outline of this structure by manually tracing the contour on one or more of the image slices. Similarly, extraction of the facial nerve may also require manual intervention from the user, such as by manually identifying the outline of the facial nerve in each image slice in which this structure is present.

While the above described two level image segmentation is preferred, any method which provides accurate delineation of the neighboring structures in a region of interest can be used in the practice of the present treatment planning method. One such technique is described in the article "On segmentation of colon lumen for virtual colonoscopy" by Liang et al., Proceedings of SPIE Medical Imaging, pp 270-278, February 1999, San Diego.

Once image segmentation is performed, 3D image generation can be performed for each of the segmented objects using a number of known techniques, such as the Marching Cubes algorithm, which reconstructs the outer polygonal surface. However, because of the complexity of the structures which make up the ear, interactive rendering of all polygons in the display for each change to a portion of the display is processor intense and unduly costly. As more colors and surfaces are delineated in the displayed image, this burden increases. To minimize the processing overhead, the volume image dataset can be stored in a partitioned data structure, such as a binary space-partitioning (BSP) tree, in which the large dataset is parsed into relatively small portions which are stored in leaf nodes of the data structure. By identifying which leaf nodes are effected by any given operation, and only performing operations, such as Constructive Solid Geometry (CSG) operations, on the effected leaf nodes, the processing burden for interactive operations can be significantly reduced. As will be set forth in more detail below, the processing burden can be further reduced by use of a level of detail (LOD) rendering mode and/or a wavelet transformation to reduce the data volume.

An exemplary BSP-tree construction will be described in connection with FIGS. 4 and 5. The BSP-tree uses the original volume image data as the root node of the tree. This is represented in step 440 of FIG. 4 by (0,0,0, dim x, dim y, dim z, $n_p$) where the parameters dim x, dim y, and dim z are the resolution of the original dataset and $n_p$ is the total number of polygons within the original dataset. A binary subdivision is performed on this node that geometrically divides the node into two sub-nodes if $n_p$ is greater than a predetermined constant $n_0$. The binary subdivision operation is recursively applied to each sub-node until the number of polygons in the sub-nodes is less than or equal to the value of $n_0$. At this point, the resulting sub-nodes are defined as leaves in the constructed tree data structure.

Figure 4:
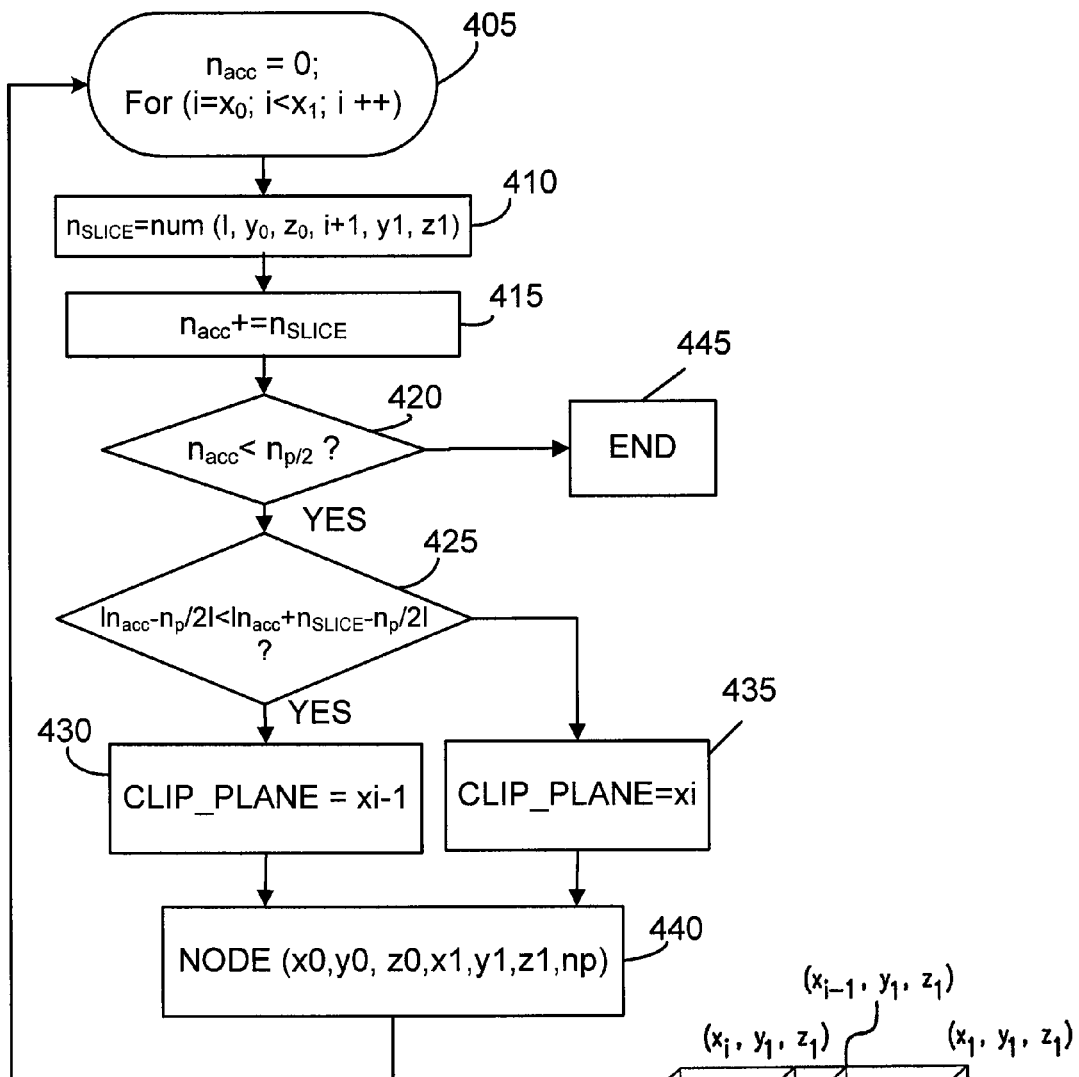
FIG. 4 is a flowchart illustrating an exemplary subroutine for generating a binary space partitioning (BSP) tree data structure used for storing and manipulating image data in the present method.
Figure 5:
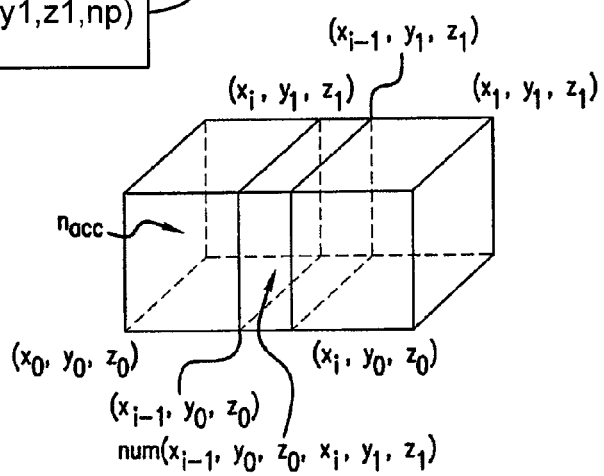
FIG. 5 is a pictorial representation of a geometrical subdivision process of a node in the BSP-tree.

The node subdivision which is used in the tree generation process is illustrated in the algorithm illustrated in the flowchart of FIG. 4 and the pictorial diagram of FIG. 5. Referring to FIG. 5, (x0, y0, z0, x1, y1, z1, $n_p$) represents a node in the tree in Cartesian space. In this specific example, $n_0$ is defined as $n_{p/2}$. The subdivision process occurs by dividing the node using a Cartesian plane which is perpendicular to the longest axis of the given node. In the case of FIG. 5, the longest axis of the node shown is along the X axis. As illustrated in FIG. 4, Steps 405-440, the position at which the node will be bifurcated is determined by accumulating a number of polygons slice by slice through the volume in the node area along the X axis until the accumulated number, $n_{acc}$, reaches a value of $n_{p/2}$, when processing is complete at Step 445. This exemplary construction of the BSP tree results in a substantially balanced tree structure, both in tree depth and the number of polygons in the resulting leaf nodes.

Figure 6:
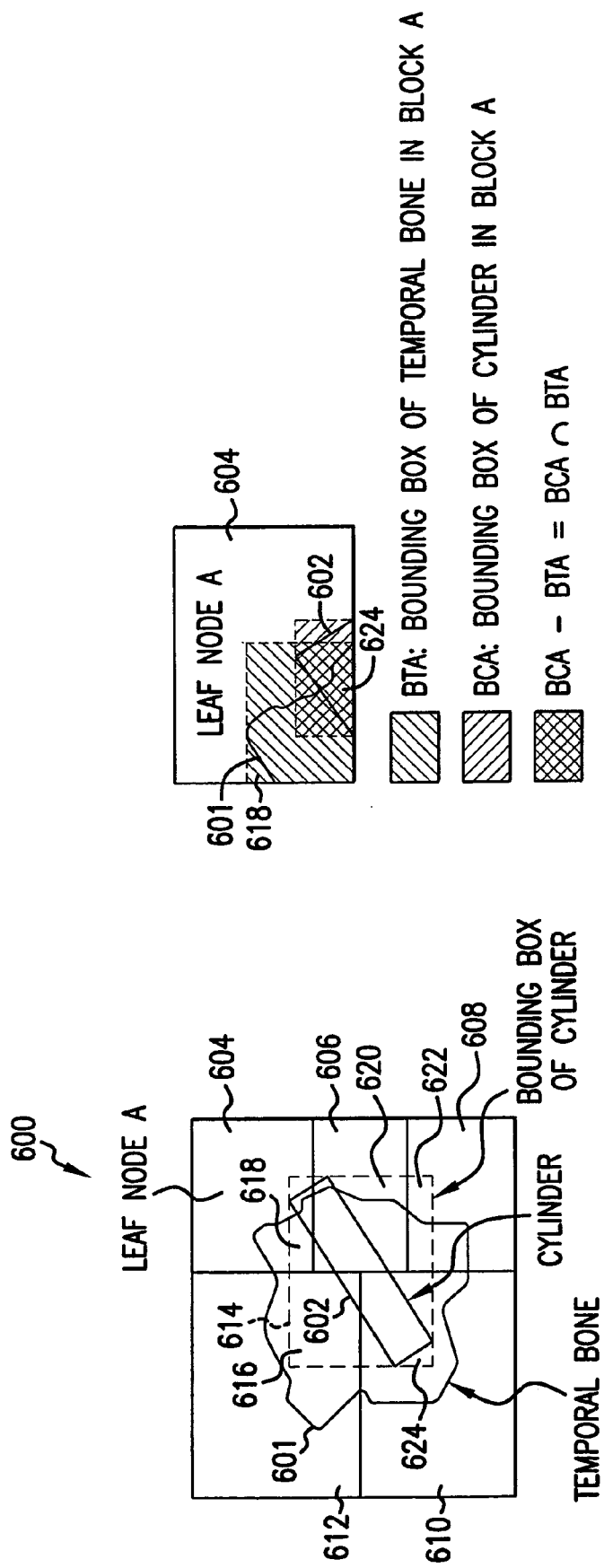
FIG. 6A is a schematic diagram of an exemplary image (illustrated in 2D) partitioned by a number of leaf nodes.
FIG. 6B is a detail of one leaf node partition from FIG. 6A, further illustrating a region of overlap between a virtual cylinder placed in the image and the underlying tissue in the image.

FIG. 6A illustrates the placement of the virtual cylinder 602 of Step 310, represented as a voxel based volume, into a portion of the volume image 600 including a portion of the temporal bone 601. For the sake of simplicity, the drawing in FIGS. 6A and 6B are illustrated in two dimensions, however, it will be appreciated that the image is a 3D voxel representation. The image 600 is illustrated as partitioned by the leaf nodes 604, 606, 608, 610 and 612 of the BSP data structure. To determine the effect of the placement of cylinder 602, the leaf nodes which are effected by the placement of the cylinder 602 are identified, then a voxel-based constructive solid geometry (CSG) subtraction operation is performed.

Figure 7:
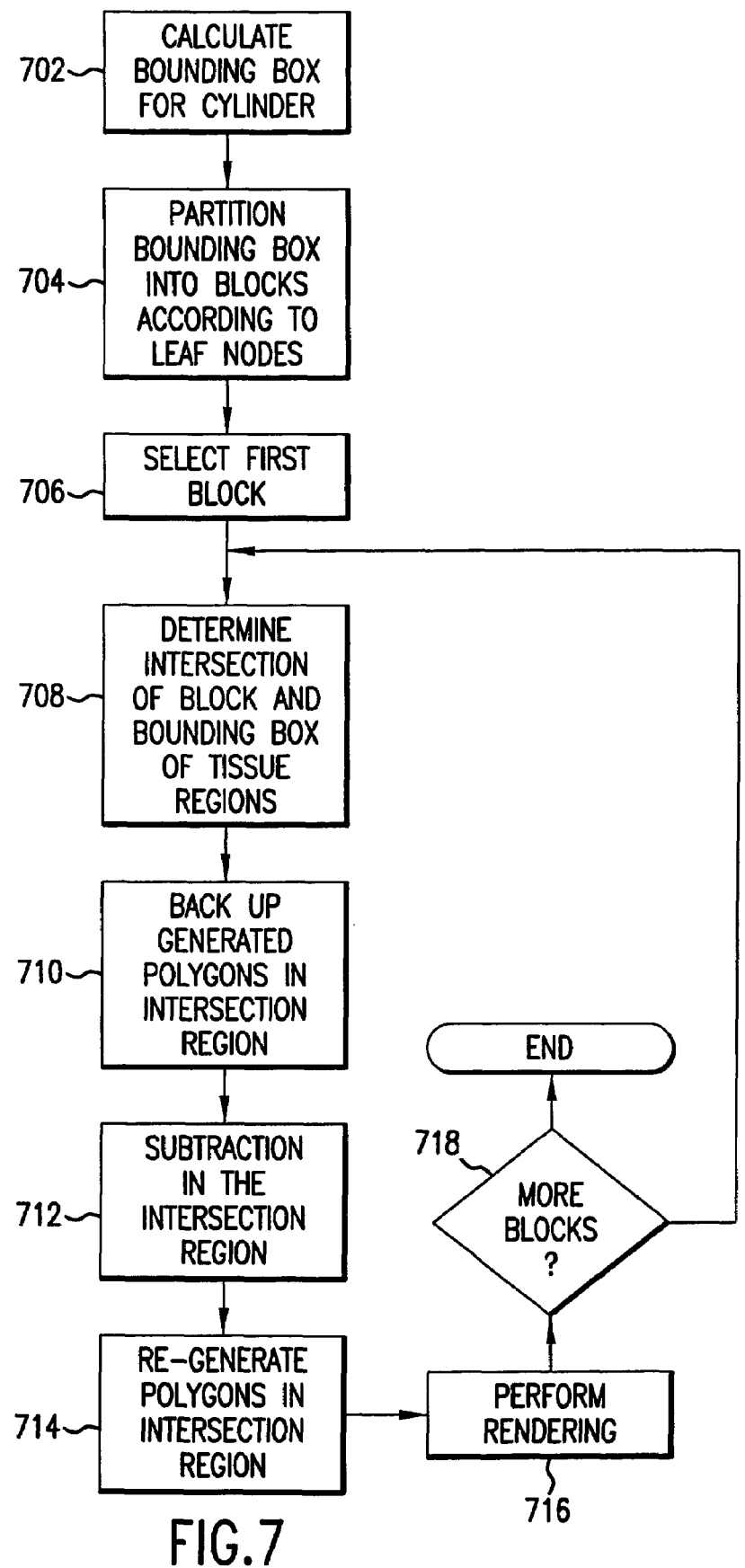
FIG. 7 is a flow chart illustrating a voxel-based constructive solid geometry (CSG) subtraction operation which is employed in the virtual surgery operation of the present method.

Referring to FIG. 7, to identify the leaf nodes which are effected by the placement of the cylinder 602, a minimum, axis aligned bounding box 614 is generated which encompasses the cylinder (step 702). Next, the bounding box 614 is partitioned into blocks 616, 618, 620, 622, 624 according to the boundaries of the leaf nodes (step 704). A first block is selected (step 706) and the intersection 624 of the cylinder 602 and temporal bone 601 within the selected block 604 is determined (step 708). It is within this intersection region 624 that a CSG subtraction operation and voxel regeneration operation will take place. Because the voxels in the intersection region 624 within the block will be altered by a CSG subtraction operation, the original voxels are stored as a backup so that the last image can be restored, for example, if the cylinder 602 is subsequently repositioned (step 710). Once the original values are stored in a back-up memory location, a subtraction of the voxel values of the cylinder 602 from the voxel values of the temporal bone 601 in the intersection region 624 determines the shape after a drilling operation (step 712). A regeneration process in the area of intersection region provides the new surface description (step 714). From the new surface description, the new surface can be rendered in the 3D image of the block, such as by using a Marching Cubes algorithm (step 716). The process from step 708 to step 716 is repeated for each block within the bounding box 614 (step 718).

To further manage the data in a manner which allows efficient navigation and viewing of the virtual organs being displayed, a level-of-detail (LOD) rendering mode can be used. In the LOD method, a reduced dataset is generated from the full volume data set. For example, the 512×512×256 full dataset can be reduced to a 64×64×32 reduced volume dataset using a multi-resolution decomposition with three levels of thresholding. Next, polygons used to render the volume images in both the enlarged and reduced volume datasets can be extracted. A traditional Marching Cubes method can be used to extract polygons to fit the surface of the object.

During navigation or viewing, polygon culling can be applied by first removing those leaf nodes that are completely outside the field-of-view from current processing operations. The remaining polygons are recalled from the BSP tree, ordered and rendered in those spaces which were not culled. Thus, the BSP tree provides an effective tool for selecting a relevant portion of the dataset for a particular navigation or display operation.

The enlarged and reduced datasets are cooperatively used in a two level LOD rendering mode. If a user is interacting with the object being displayed, such as rotating, shifting or effecting other changes in the field of view, the polygons from the reduced dataset (64-sized) are rendered. Because of the significantly lower number of polygons involved, interaction with the reduced dataset volume can be performed faster and with less processing overhead. The tradeoff for the increased speed is reduced image resolution. If there is no interaction from the user after a predetermined time period, the polygons of the enlarged dataset (512-sized) are selected from the BSP tree and are rendered to provide a high resolution image of the current field of view As noted above, when a large dataset is involved, it may be required, or at least desirable, to reduce the size of the dataset to speed up processing and reduce processing cost. Noting that the tree structure can be preserved within a range of scales, the large volume can be shrunk to a smaller scale space for structure analysis.

A shrinking method based on multiresolution analysis theory can be used. The input data is the stack of binary images of the same size which can be obtained from the segmentation results of the CT or MRI scan. The x-direction is taken along the slice image width, the y-direction is along the slice image height, and the z-direction is along the direction of slice by slice. The foreground voxels in the tree volume are set to value of 128 (maximum) and the background voxels are set to value 0 (minimum). A Daubechies' bi-orthogonal wavelet transform with all rational coefficients can be employed. This one-dimensional (ID) discrete wavelet transformation (DWT) is first applied along to the x-direction row by row. From application of the DWT only the lower frequency components are retained and packed. The computation is preferably implemented in floating points. Noting that the DWT is applied to the binary signal, there are two kinds of nonzero coefficients which result in the lower frequency component. The first is of value 128 and this kind of coefficients are located in the interior of the volume. The second is of a value not equal to 128 and these coefficients locate the boundary of the volume.

The coefficients of the second kind are compared against a predetermined threshold value. If its absolute value is larger than a pre-set threshold T1, the value of the coefficient is set to 128; otherwise, it is set to 0. This results in a stack of binary images with a row size of half of the original dataset. The same DWT is then applied to the resulting dataset along the y-direction column by column, where the similar thresholding is employed to the lower frequency components. The result is again a stack of binary images, but now with both half row and column size as compared to the original dataset. Finally, the DWT is applied to the last result along the z-direction and the lower frequency components are retained. This step completes the first level decomposition.

The resulting dataset of the first level decomposition is of half size in all three directions as compared to the original dataset. If the shrinking procedure stops at this level, the finial thresholding is applied. It revalues those coefficients of non-zero and non-128 value. If the absolute value of this kind of coefficient is larger than a pre-set threshold T2, it will be revalued as 128; otherwise, it is revalued as 0. If further shrinking is needed, the same thresholding algorithm is applied with the threshold T1. Further shrinking proceeds as previously described, but is applied to the dataset shrunk at the last previous level. The decomposition procedure can be recursively applied until the resulting volume meets the desired reduced data volume. In the case where the slice images are of 512×512 pixel size, the maximum decomposition level is usually three, resulting in a 64×64 reduced pixel size.

The volume is isotropically shrank in all directions with the presented method. The two pre-set thresholds, T1 and T2, are used to control the degree of shrinking. If the volume is significantly over shrunk, connectivity may be lost in the reduced volume. If it is over shrunk to a leaser degree, two separate branches may merge into one branch in the reduced volume dataset. The larger the two threshold values, the thinner the reduced volume is. The range of those two thresholds is [0, r×128], where 0<r<1. Preferably, the range for virtual endoscopy is r∈(0.08, 0.28) for T1 and r∈(0.7, 0.98) for T2. The exact determination is dependant on the feature size of the particular application and is selected to achieve reduction while retaining the fidelity of the structure information in the shrunk volume.

To determine if a warning should be generated in step 315 (FIG. 3), each block 616, 618, 620, 622, 624 can be evaluated to determine if tissue types, other than that of the temporal bone, are proximate the current location of the cylinder 602. If the cylinder is within a predetermined threshold distance of a critical structure, a warning can be generated. For example, if the proposed cylinder location is within 1-2 mm of the facial nerve, a warning can be provided. The warning can take the form of a text message, an audible signal, or by highlighting the area of risk in the image for the user, such as by use of a special color or by automatically magnifying the region for closer examination by the user.

While the invention has been described in detail in connection with the treatment planning for aural atresia, it is generally applicable to numerous treatment planning operations both in the ear and elsewhere in the body. For example, in the case of angioplasty, the surgeon inserts a catheter into an occluded artery and inflates a balloon at the end of the catheter to force the occluded artery open and to expand a stent which maintains the opening. While this has become a common procedure, it is not without risk. For example, the arterial occlusion is generally related to a build up of plaque and fatty deposits on the arterial wall. If a portion of these deposits are dislodged during the angioplasty process, there is a risk of stroke and other complications. Using the present method of treatment planning, the artery can be imaged and, through image segmentation, the quantity and nature of the plaque deposits can be determined. The severity of the occlusion can be viewed by the surgeon who can navigate in the 3D image within the artery. A virtual intervention can then be performed, i.e., placing a virtual catheter within the arterial volume and expanding a virtual stent, and the results observed. If problems are observed, the user can then alter the course of treatment to minimize the risk. Unlike the case of aural atresia, in this case, the virtual catheter would require a dynamic model that conforms to the contours of the interior surface of the arterial wall. Such a model is analogous to the force field model previously used in guiding a virtual camera along a fly path in performing virtual colonoscopy.

Similarly, the present method is applicable to treatment planning for the formation and implantation of a stent graft for treating abdominal aortic aneurisms. The 3D imaging can be used to determine the size, location and nature of the aneurism. In addition, using image segmentation, the quality of the arterial wall can be determined by analyzing the composition of the arterial wall to determine the degree of plaque build up and stenosis. A virtual stent graft can be modeled to fit in the region of the AAA and the graft can be inserted into the 3D image. Alternatively, the surgical removal of plaque can be the modeled intervention. In either case, the user can navigate within the treated region to visualize the results of the proposed intervention.

Another application of the present method of treatment planning is in a virtual biopsy. In this case, an organ, such as the prostate, breasts or lungs can be scanned and rendered as a segmented 3D image. Preferably, the image segmentation process at least partially highlights those portions of the organ of interest which have a high likelihood of containing cancerous tissue. A virtual cylinder can be placed into this region to simulate the insertion of a biopsy needle. The position, size and shape of the cylinder can be optimized by the user to insure that at least part of the suspicious region is within the volume of the cylinder. The region within the virtual cylinder can then be withdrawn from the organ and displayed in a different window of the display for further analysis.

Known volume rendering techniques use one or more defined transfer functions to map different ranges of sample values of the original volume data to different colors, opacities and other displayable parameters for navigation and viewing. During navigation, the selected transfer function generally assigns maximum opacity to the wall of the object being viewed. However, once a suspicious area is detected during virtual examination and is extracted during the virtual biopsy intervention, the physician can interactively change the transfer function assigned during the volume rendering procedure such that the outer surface being viewed becomes substantially transparent, allowing the interior structure of the region to be viewed. Using a number of predetermined transfer functions, the suspicious area can be viewed at a number of different depths, with varying degrees of opacity assigned throughout the process. In addition, the shape of the region and texture of the region undergoing virtual biopsy can be analyzed to determine a likelihood of cancerous tissue in the region being biopsied.

Although the present invention has been described in connection with specific exemplary embodiments, it should be understood that various changes, substitutions and alterations can be made to the disclosed embodiments without departing from the spirit and scope of the invention as set forth in the appended claims.

The invention claimed is:

1. A method of computer aided treatment planning, performed on a computer system, the method comprising:
    acquiring a set of 2D images of a region of a patient to be treated;
    converting said 2D images to a voxel based dataset of the region;
    storing at least a portion of the voxel based dataset in a partitioned dataset as a binary space partitioning tree having a plurality of leaf nodes;
    generating a three dimensional image of the region of the patient to be treated from the voxel based dataset, the region including at least one anatomical structure for which treatment is contemplated;
    identifying the leaf nodes which are effected by the application of a virtual intervention;
    applying said intervention to the effected leaf nodes and re-generating the portions of the three dimensional image associated with the effected leaf nodes;
    determining the effect of said intervention;
    modifying the intervention for improved treatment results; and
    navigating within the three dimensional image in the area where the intervention is applied to visualize the results of the intervention.

2. The method of computer aided treatment planning according to claim 1, wherein the region includes the ear and the at least one anatomical structure includes at least one of the temporal bone, facial nerve, and stapes.

3. The method of computer aided treatment planning according to claim 2, wherein the virtual intervention includes the placement of a virtual cylinder representing the location where an external auditory canal may be formed.

4. The method of computer aided treatment planning according to claim 3, wherein the step of determining the effect of the virtual intervention includes determining the proximity of the virtual cylinder to anatomical structures of the ear and providing a warning if said proximity is less than a predetermined threshold distance.

5. The method of computer aided treatment planning according to claim 4, wherein the step of modifying the intervention includes changing the position of the virtual cylinder.

6. The method of computer aided treatment planning according to claim 4, wherein the step of modifying the intervention includes changing the diameter of the virtual cylinder.

7. The method of computer aided treatment planning according to claim 4, wherein the step of modifying the intervention includes changing the length of the virtual cylinder.

8. The method of computer aided treatment planning according to claim 3, further comprising the steps of virtually removing the volume within the virtual cylinder and navigating through the region in the three dimensional image.

9. The method of computer aided treatment planning according to claim 1, further comprising the step of saving the results of the virtual intervention in computer readable storage, receiving image data from an actual intervention, and comparing the results of the actual intervention to the patient to be treated to the saved results of the virtual intervention.

10. The method of computer aided treatment planning according to claim 1, further comprising the steps:
    performing automated segmentation of the voxel based dataset to identify features; and manually editing and extracting the automated segmented features, wherein the generating operation employs both the voxel based dataset and said identified features.

11. The method of computer aided treatment planning according to claim 10, wherein said generating operation further comprises a level-of-detail operation and a constructive solid geometry operation.

12. A method of computer aided treatment planning, performed on a computer system, the method comprising:
acquiring a voxel based dataset of a region of a patient be treated, the region including at least one anatomical structure for which treatment is contemplated;
storing the voxel based dataset in a partitioned dataset as a binary space partitioning tree having a plurality of leaf nodes;
generating a three dimensional image of region from the voxel based dataset;
identifying the leaf nodes which are effected by the application of a virtual intervention;
applying a virtual intervention to the effected leaf nodes and re-generating the portions of the three dimensional image associated with the effected leaf nodes;
analyzing the intervention and automatically generating a warning indication if said intervention is with in a predetermined distance of a critical structure; and
modifying the intervention to eliminate said warning.

13. The method of computer aided treatment planning according to claim 12, wherein the intervention is performed by a tool having a tool contour and wherein said step of applying the intervention includes applying a generalized virtual cylinder substantially conforming to the tool contour to the region.

14. The method of computer aided treatment planning according to claim 13, wherein the tool has elastic properties and the generalized virtual cylinder is further modeled as a deformable object.

15. The method of computer aided treatment planning according to claim 14, wherein the intervention is the placement of an arterial stent and wherein the tool is a balloon catheter.

16. The method of computer aided treatment planning according to claim 15, wherein the step of generating a three dimensional image of a region includes an image segmentation step for differentiating the tissue of arterial wall from plaque build up on the arterial wall.

17. The method of computer aided treatment planning according to claim 16, further comprising a step of quantifying components of plaque build up on the arterial wall.

18. The method of computer aided treatment planning according to claim 14, wherein the intervention is the removal of plaque from an arterial surface and the step of applying the virtual intervention further comprises:
generating a virtual model of the plaque with size and components within the arterial volume;
applying a generalized virtual cylinder in the proposed location of the artery; and
placing the virtual model of the plaque within the volume of the generalized virtual cylinder.

19. The method of computer aided treatment planning according to claim 18, wherein the step of modifying the intervention includes altering at least one of the size, shape and position of the generalized virtual cylinder.

20. The method of computer aided treatment planning according to claim 18, wherein the warning is generated if the placement of the generalized virtual cylinder will impinge on nearby anatomic structures.

21. The method of computer aided treatment planning according to claim 18 wherein the step of modifying the intervention includes altering the virtual model of the plaque.

22. The method of computer aided treatment planning according to claim 13, wherein the intervention is the placement of a prosthetic implant and the step of applying the virtual intervention includes:
generating a virtual model of the prosthetic implant;
applying a generalized virtual cylinder in the proposed location of the implant; and
placing the virtual model of the prosthetic implant within the volume of the generalized virtual cylinder.

23. The method of computer aided treatment planning according to claim 22, wherein the step of modifying the intervention includes altering at least one of the size, shape and position of the generalized virtual cylinder.

24. The method of computer aided treatment planning according to claim 23, wherein the warning is generated if the placement of the generalized virtual cylinder will impinge on nearby anatomic structures.

25. The method of computer aided treatment planning according to claim 24, wherein the step of modifying the intervention includes altering the virtual model of the prosthetic implant.

26. The method of computer aided treatment planning according to claim 25, wherein the implant is a stent graft, and wherein the virtual intervention includes placing a virtual model of a stent graft within a virtual model of an aortic blood lumen.

27. The method of computer aided treatment planning according to claim 26, wherein the step of modifying the intervention includes altering the virtual model of the stent graft.

28. The method of computer aided treatment planning according to claim 25, further comprising a step of providing the virtual model to a computer assisted system for fabricating the prosthetic implant.

29. The method of computer aided treatment planning according to claim 12, wherein the region includes the ear and the at least one anatomical structure includes at least one of the temporal bone, facial nerve, ossicles and stapes.

30. The method of computer aided treatment planning according to claim 29, wherein the virtual intervention includes the placement of a virtual cylinder representing the location where an external auditory canal may be formed.

31. The method of computer aided treatment planning according to claim 30, wherein the step of analyzing the effect of the virtual intervention includes determining the proximity of the virtual cylinder to anatomical structures of the ear and said warning is provided if said proximity is less than a predetermined threshold distance.

32. The method of computer aided treatment planning according to claim 31, wherein the step of modifying the intervention includes changing the position of the virtual cylinder.

33. The method of computer aided treatment planning according to claim 31, wherein the step of modifying the intervention includes changing the diameter of the virtual cylinder.

34. The method of computer aided treatment planning according to claim 31, wherein the step of modifying the intervention includes changing the length of the virtual cylinder.

35. The method of computer aided treatment planning according to claim 30, further comprising the steps of virtually removing the volume within the virtual cylinder and navigating through the region in the three dimensional image.

36. The method of computer aided treatment planning according to claim 35, further comprising the step of saving the treatment plan in computer readable media and comparing the treatment plan to the results after intervention.

37. The method of computer aided treatment planning according to claim 12, wherein the intervention is the placement of a virtual biopsy needle into a targeted position within the region, and wherein said warning is provided if said virtual biopsy needle is outside the targeted position.

38. The method of computer aided treatment planning according to claim 12, wherein the intervention is the placement of a virtual biopsy needle into a targeted position within the region, and wherein said warning is provided if said virtual biopsy needle may damage any anatomical structure proximate the targeted position.

39. The method of computer aided treatment planning according to claim 38, wherein the targeted region includes at least one of a prostate, breast and a lung.

40. A system for computer aided treatment planning comprising:
   an input device for receiving acquired image data from a patient;
   a processor, said processor being operatively coupled to the input device, receiving the image data and generating a voxel based dataset representing at least a portion of the image data;
   a memory device operatively coupled to said processor and storing at least a portion of the voxel based dataset in a partitioned dataset as a binary space partitioning tree having a plurality of leaf nodes;
   a display operatively coupled to said processor and providing a three dimensional representation of the at least a portion of the image data from said voxel based dataset;
   a user interface device operatively coupled to the processor, the three dimensional representation being manipulated in response to input by a user via said user interface device; and
   a memory device having a computer program stored therein, said computer program directing the processor to perform the steps:
      applying a virtual intervention in a region of said three dimensional representation in response to a signal from said user interface device, wherein the applying operation further comprises identifying those leaf nodes which are effected by said intervention, applying said intervention to the effected leaf nodes; and re-generating only the portions of the three dimensional representation associated with the effected leaf nodes;
      analyzing the intervention and automatically generating a warning indication if said intervention is within a predetermined distance of a critical structure; and
      modifying the intervention to eliminate said warning.

* * * * *